Figure 4:
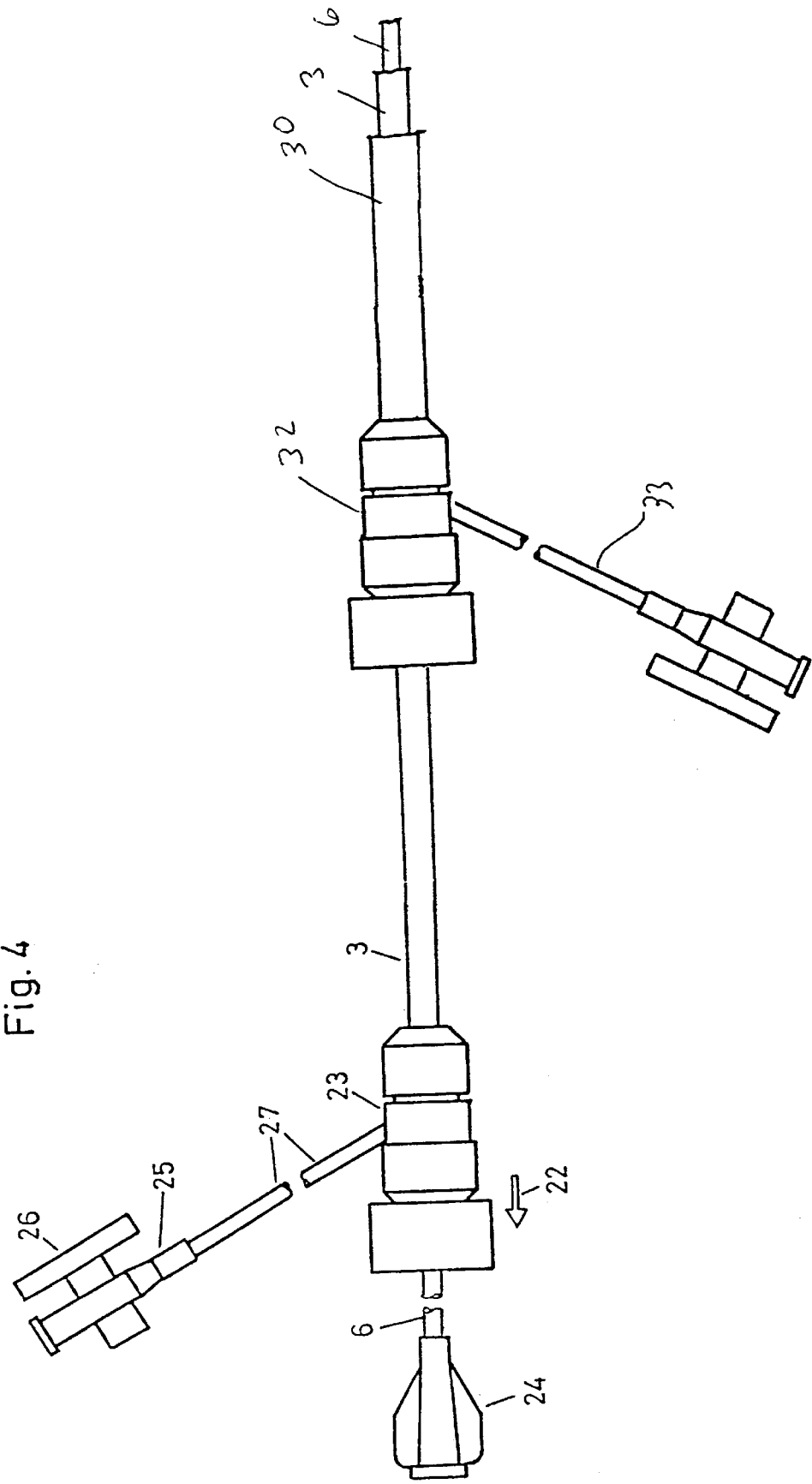

United States Patent
Lukic et al.

[11] Patent Number: 5,919,204
[45] Date of Patent: Jul. 6, 1999

[54] APPARATUS FOR RELEASING A SELF-EXPANDING ENDOPROSTHESIS

[75] Inventors: Goran Lukic, Bulach; Eugen Hofmann, Zürich, both of Switzerland

[73] Assignee: Schneider (Europe) A.G., Bulach, Switzerland

[21] Appl. No.: 08/249,821

[22] Filed: May 26, 1994

[30] Foreign Application Priority Data

Jun. 2, 1993 [EP] European Pat. Off. .............. 93810398

[51] Int. Cl.⁶ .......................... A61B 17/00; A61M 29/00
[52] U.S. Cl. .................. 606/198; 623/1; 623/12
[58] Field of Search .................... 606/191, 194, 606/198, 200; 623/1, 12; 128/898, 899

[56] References Cited

U.S. PATENT DOCUMENTS

| | | |
|---|---|---|
| 4,665,918 | 5/1987 | Garza et al. . |
| 4,732,152 | 3/1988 | Wallsten et al. . |
| 4,768,507 | 9/1988 | Fischell et al. . |
| 4,893,623 | 1/1990 | Rosenbluth . |
| 5,026,377 | 6/1991 | Burton et al. . |
| 5,201,757 | 4/1993 | Heyn et al. . |
| 5,591,172 | 1/1997 | Bachmann et al. . |

FOREIGN PATENT DOCUMENTS 0350043  1/1990  European Pat. Off. .

*Primary Examiner*—William Lewis
*Attorney, Agent, or Firm*—Philip C. Strassburger

[57] ABSTRACT

When installed in the device, the endoprosthesis is compressed radially and located in a cylindrical chamber (14), one proximal area (A) of this endoprosthesis lies within a first outer catheter (3) and a second distal area (B) is in a second outer catheter (30). In order to release the endoprosthesis (1) in a vessel (11), for example, the second outer catheter (30) is first retracted. The endoprosthesis (1) is then held in the first outer catheter (3) by friction and can be re-folded and thus repositioned by advancing the second outer catheter (30). Finally, the endoprosthesis (1) is released by retracting the first outer catheter (3). Because the friction is distributed over at least two outer catheters (3, 30), even endoprostheses (1) that generate a high level of friction on the outer catheter, for example because of a coating, of greater expansion force, or because of great length, can be released.

12 Claims, 3 Drawing Sheets

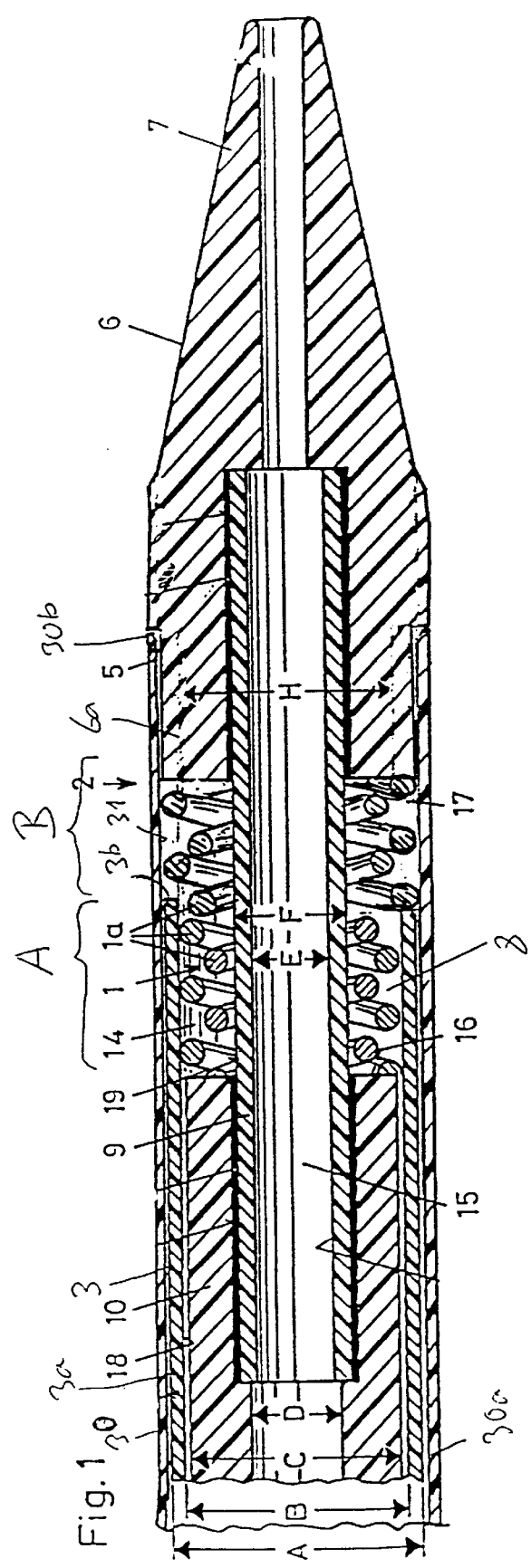

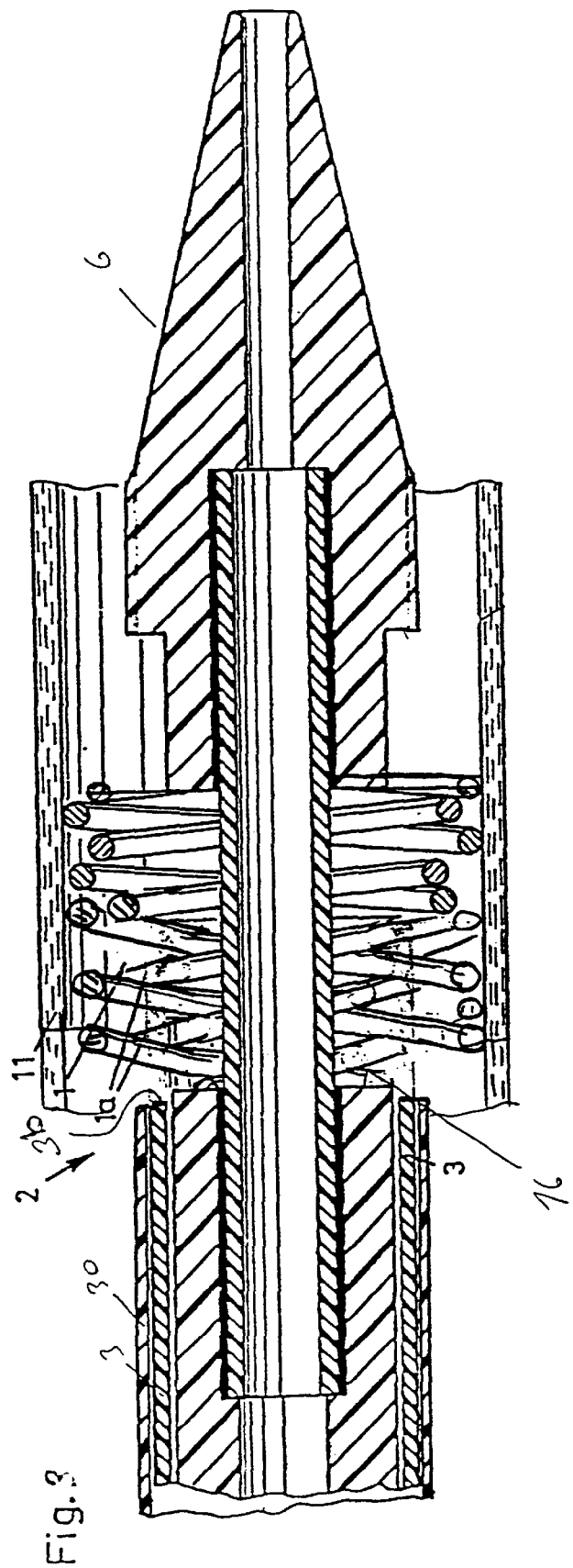

APPARATUS FOR RELEASING A SELF-EXPANDING ENDOPROSTHESIS

The present invention relates to an apparatus for releasing a self-expanding endoprosthesis, with an elongated and flexible outer catheter with a distal end and a proximal end and with an elongated and flexible inner catheter that is arranged coaxially to the outer catheter, this inner catheter having at its distal end a tip and proximally to this a means to accommodate the endoprosthesis, it being possible to slide the outer catheter in its longitudinal direction over the means to fix the endoprosthesis and retract it over the means in order to release the endoprosthesis.

A device of this type, as well as endoprostheses, have been described, for example, in U.S. Pat. No. 5,026,377. Using this device, an endoprosthesis, which is also referred to as a stent or vessel support, can be implanted. Such implantation can, for example, be carried out after balloon dilation of a stenosis in order to prevent recidivistic stenosis. However, they can also be implanted in the urinary tract, bile ducts, or veins in order to prevent blockage of such vessels. The endoprostheses may, for example, be in the form of a tube-like woven mesh or web of stainless-steel wire. Using such a device, an endoprosthesis is emplaced at the required position when compressed, and is then released by retracting the tubular outer catheter. When this is done, the endoprosthesis expands radially outwards automatically, when it also becomes shorter, and presses against the wall of the vessel.

The device referred to has proved itself in practical use.

However, using such a device, it is difficult to release endoprostheses that have an outer covering and which are also known as so-called "covered stents," which have important advantages. In the same way, releasing very long endoprostheses and those having great expansion tension can cause difficulties. Finally, endoprostheses that incorporate wires with a porous surface can only be released with difficulty. These difficulties that are encountered when releasing such endoprostheses are caused, particularly, by the fact that the outer catheter cannot be retracted or can only be retracted by using a comparatively large amount of force.

It is the task of the present invention to create a device of the type described, which avoids the difficulties described above and which, in addition, is simple to operate and reliable.

In a device of this kind, this problem has been solved in that a second outer catheter is arranged coaxially around the outside of the outer catheter such that it can be slid longitudinally on the first outer catheter; in that with an endoprosthesis installed, the distal end of the second outer catheter extends distally beyond the first outer catheter in such a way that a distal area of the endoprosthesis is pressed against an inner side of the second outer catheter and a proximal area is pressed against the inner side of the first outer catheter; in order to release the endoprosthesis, the second outer catheter and the first outer catheter can be retracted from the endoprosthesis on the inner catheter. In the device according to the present invention, in order to release the endoprosthesis, first the second outer catheter and then the first outer catheter are retracted. Since, at this point, only a part of the endoprosthesis is lying against the second outer catheter when the second outer catheter is retracted, only the friction of this part of the endoprosthesis has to be overcome. When the first outer catheter is retracted all that is then required is to overcome the friction of the other area of the endoprosthesis. The total friction of the outside of the endoprosthesis is thus distributed over the two outer catheters. Since the requirements for strength that are imposed on the second outer catheter are comparatively low, small wall thicknesses will be sufficient so that the increase in the diameter of the device caused by the second outer catheter is correspondingly small. Apart from solving the original problem, the device according to the present invention also has the important advantage that once the second outer catheter has been retracted, the endoprosthesis is held in the first outer catheter and by advancing the second outer catheter, the endoprosthesis can be folded once again and thus either repositioned or removed completely from the vessel. Thus, the device according to the present invention brings an important advantage when implanting conventional endoprostheses. In addition, it has been found particularly simple to install the endoprosthesis. Additional advantageous features are described in the secondary claims, in the description that follows, and in the drawings.

One embodiment of the device according to the present invention will be described in greater detail below on the basis of the drawings appended hereto. These drawings show the following:

FIG. 1 a longitudinal section through the distal end of a device according to the present invention, the endoprosthesis being installed in the device;

FIG. 2 the distal end, as in FIG. 1, this being shown inserted in a vessel, the endoprosthesis being partially released;

FIG. 3 a cross-section as in FIG. 2, with the endoprosthesis completely released;

FIG. 4 a view of the proximal end of the device.

FIG. 1 shows a device 2 according to the present invention in which an endoprosthesis 1 is installed. The endoprosthesis 1 is woven, for example, from stainless-steel wires 1a and can also be provided with an extensible sleeve (not shown herein). It is, of course, to be understood that the length of the endoprosthesis 1 can be varied according to the application that is intended and this length can, in particular, be significantly greater than is shown here. In a proximal area A the complete periphery of the endoprosthesis 1 is covered by a distal area of a first outer catheter 3 and in a distal area B is covered by a second outer catheter 30. The two outer catheters 3 and 30 both have a long flexible tube section 3a, 30a, respectively, and each of these is provided with a distal opening 3b, 30b, respectively. Thus, in an area A the outer side of the endoprosthesis 1 is pressed under tension against the inner side 18 of the first outer catheter 3 and in an area B is similarly pressed under tension against the inner side 31 of the second outer catheter 30. Both outer catheters 3 and 30 prevent any radial expansion of the endoprosthesis 1.

A flexible inner catheter 6 is installed in a continuous lumen of the first outer catheter 3 and this inner catheter 6 can incorporate a continuous lumen 15 to accommodate a guide wire (not shown herein). It is preferred that the inner catheter 6 has a flexible tip 7, an intermediate section 9 and a tube section 10 that is arranged proximally to the intermediate section 9. The flexible intermediate section 9 is cylindrical on the outside and is of an outside diameter F that is smaller than the outside diameter C of the tube section 10 and is also smaller than the outside diameter H of the tip 7. Cross-sectional surfaces 16 and 17 of the tube 10 that are arranged so as to be spaced apart and of the tip 7, and the inner sides 18 and 31 of the outer catheters 3, 30, respectively, and a cylindrical outer side 19 of the intermediate section 9 form a hollow cylindrical chamber 14 in which the endoprosthesis 1 is accommodated in the compressed state. Within the chamber 14, the endoprosthesis 1 is fixed in the longitudinal direction by the surfaces 16 and 17 and on the two outer catheters 3 and 30 by friction. However, in place of the chamber 14 it is also possible to fix the endoprosthesis 1 axially on the inner catheter 6 using other means, this being done in the known manner.

An extension 6a of the tip 7 fits in the distal end of the second outer catheter 30 and a shoulder 5 of this lies against the opening 30b of this catheter. As can be seen, the shoulder 5 extends beyond the opening 30b of the outer catheter. This prevents the outer catheter 30 damaging the vessel 11 when the device is inserted into it.

As is shown in FIG. 4, at the proximal end the inner catheter 6 is provided with a connector 24 that can be used for injecting contrasting agent or to insert a guidewire. The first outer catheter 3 is connected at its proximal end to a connecting and sealing piece 23 that incorporates a seal (not shown herein) that lies on the inner catheter 6 in such a way that it can slide. The connector and sealing piece 23 is provided in the known manner with a branch 25 and a tap 26 and with a flexible tube 27, the tube 27 being connected with the lumen 8 of the first outer catheter 3. The second outer catheter 30 is similarly connected at its proximal end to a connector and sealing piece 32 and this can be configured identically to the piece 23 although it is made correspondingly larger in order to match the larger outside diameter of the catheter 30. A corresponding tube 33 is connected with the lumen of the second outer catheter 30. Thus, the first outer catheter 3 can be displaced telescopically in the longitudinal direction on the inner catheter 6, and the second outer catheter 30 can similarly be displaced telescopically on the first outer catheter 3. The whole length of the tube 30a of the second outer catheter 30 can be slid on the first outer catheter 3 and the strength requirements imposed on the second outer catheter 30 are thus comparatively small.

The device according to the present invention is used as follows. In order to install the endoprosthesis 1, this is slid onto the inner catheter 6, and the outer catheters 3 and 30 are retracted at least as far as a surface 16. By advancing the first outer catheter 3 over the endoprosthesis 1 and then, by advancing the second outer catheter 30, the endoprosthesis 1 is folded and compressed until finally it is fixed in the device as shown in FIG. 1 and the opening 30b lies against the shoulder 5 of the tip 7.

The installed endoprosthesis is now introduced into the vessel 11 (FIG. 2) with the device 2. In order to release the endoprosthesis 1, the second outer catheter 30 is retracted at the connector and sealing piece 32 until it reaches the position that is shown in FIG. 2. This means that the endoprosthesis 1 is essentially released in the area B and can expand in this area. With the arrangement shown in FIG. 2, the endoprosthesis 1 can once again be fully compressed if the second outer catheter 30 is once again advanced into the position that is shown in FIG. 1. This is possible since, according to FIG. 2, the area A of the endoprosthesis 1 is held in position by the first outer catheter 3, by friction.

In order to release the endoprosthesis completely, starting from the arrangement shown in FIG. 2, the first outer catheter 3 is retracted until an opening lies behind the surface 16. The endoprosthesis 1 is now pressed against the inner side of the vessel 11, and supports this. Since the endoprosthesis 1 is now expanded the device 2 can be withdrawn through the endoprosthesis 1 and from the vessel 11, when the endoprosthesis 1 remains behind in the vessel 11.

The two tube sections 3a and 30a preferably of a plastic that displays comparatively good slip characteristics and which is also well suited for this purpose. It is preferred that this plastic be polytetrafluorethylene. It is also possible to use an embodiment in which more than two outer catheters are used, these being able to telescope and each in part surrounding the endoprosthesis.

We claim:

1. A device for releasing a self-expanding endoprosthesis, the device comprising:

(a) an inner catheter, (b) a first outer catheter slidably disposed at least partially about the inner catheter and having a curved inner surface;

(c) a second outer catheter slidably disposed at least partially about the first outer catheter and having a curved inner surface; and (d) a self-expanding endoprosthesis having (i) a first end portion configured within and in contact with the curved inner surface of the first outer catheter, and (ii) a second end portion configured within and in contact with the curved inner surface of the second outer catheter.

2. The device of claim 1 wherein the first outer catheter has a distal end, and the second outer catheter extends distally beyond the distal end of the first outer catheter.

3. The device of claim 2 wherein the inner catheter has a proximal end and the first and second outer catheters are adapted to slide longitudinally toward the proximal end of the inner catheter to release the endoprosthesis.

4. The device of claim 3, wherein the inner and outer catheters are independently slidable toward the proximal end of the inner catheter.

5. The device of claim 1, wherein the second outer catheter comprises a flexible tube which is secured proximally to seal the second outer catheter against the first outer catheter.

6. The device of claim 1, wherein the second outer catheter has a distal end having a circular opening.

7. The device of claim 1, wherein the inner catheter has a tip having a shoulder which extends laterally beyond the second outer catheter at its distal end.

8. The device of claim 1, wherein the inner surface of the second outer catheter is smooth at least at a distal end.

9. The device of claim 5, wherein the flexible tube comprises polytetrafluorethylene.

10. The device of claim 5, wherein the first outer catheter and the second outer catheter have essentially the same wall thicknesses.

11. The device of claim 1, wherein the inner catheter has an outer surface having a circular cylindrical recess to accommodate the endoprosthesis.

12. The device of claim 1 wherein the first outer catheter has a distal section adapted to receive a proximal end portion of the prosthesis and the second outer catheter has a proximal section adapted to receive a distal end portion of the prosthesis.

* * * * *